United States Patent
Kuhnt et al.

[11] Patent Number: 6,103,726
[45] Date of Patent: Aug. 15, 2000

[54] USE OF PYRROLOPYRIMIDINES FOR CONTROLLING PESTS

[75] Inventors: Dietmar Kuhnt, Burscheid; Klaus-Günther Tietjen, Langenfeld; Hermann Uhr, Krefeld; Robert Markert, Cologne; Ralf Tiemann, Leverkusen; Klaus Stenzel, Düsseldorf; Stefan Dutzmann, Langenfeld; Christoph Erdelen, Leichlingen; Ulrike Wachendorff-Neumann, Neuwied, all of Germany

[73] Assignee: Bayer Aktiengesellschaft, Leverkusen, Germany

[21] Appl. No.: 09/202,475

[22] PCT Filed: Jun. 9, 1997

[86] PCT No.: PCT/EP97/02990

§ 371 Date: Dec. 11, 1998

§ 102(e) Date: Dec. 11, 1998

[87] PCT Pub. No.: WO97/48280

PCT Pub. Date: Dec. 24, 1997

[30] Foreign Application Priority Data

Jun. 20, 1996 [DE] Germany .............. 196 24 603

[51] Int. Cl.[7] .................. C07D 487/04; A01N 43/90
[52] U.S. Cl. .......................... 514/258; 544/280
[58] Field of Search .................. 544/280; 514/258

[56] References Cited

FOREIGN PATENT DOCUMENTS 3436380  4/1986  Germany .

OTHER PUBLICATIONS

Renau et al., J. Med. Chem. 1996, 39, 3470–3476.
J. Med. Chem, 1995, 38, 3884–3888.
Chem. Ber., 1942, 75, p. 755.
J. Org. Chem., Oct. 1961, 26, p. 3809.
Chem. Ber., (month unavailable) 1979, 112, p. 3432.
Chem. Ber. (month unavailable) 1979, 112, 799.
Liebigs Ann. Chem. (month unavailable) 1984, pp. 273–282.
Liebigs Ann. Chem. (month unavailable) 1984, pp. 722–733.
Liebigs Ann. Chem. (month unavailable) 1985, pp. 312–320.
J. Med. Chem. (month unavailable) 1985, 28, pp. 1462–1467.
Renau et al., Chem. Abstract: 125:275786 (1996).
Altmann et al., Chem. Abstract: 127:293238 (1997).
Yamada et al., Chem. Abstract:121:230784 (1994).

*Primary Examiner*—Richard L. Raymond
*Assistant Examiner*—B Jayaram
*Attorney, Agent, or Firm*—Joseph C. Gil; Carol Marmo

[57] ABSTRACT

Pyrrolopyrimidines of formula (I) in which $R^1$, $R^2$, $R^3$, $R^4$, $R^5$ and A have the meanings given in the description, and their acid-addition salts and metal salt complexes are very highly suitable for combatting vegetable and animal pests.

Novel pyrrolopyrimidines of formula (Ia) in which $R^6$, $R^7$, $R^8$, $R^9$, $R^{10}$ and Z have the meanings given in the description, and their acid-addition salts and metal salt complexes, and a process for their production.

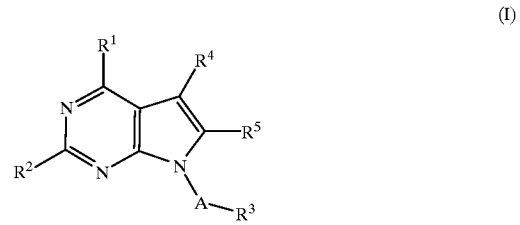

(I)

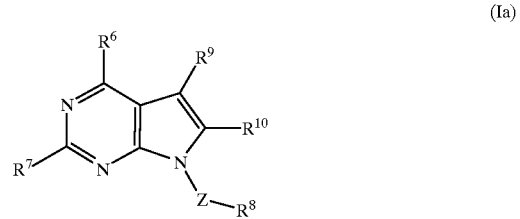

(Ia)

1 Claim, No Drawings

USE OF PYRROLOPYRIMIDINES FOR CONTROLLING PESTS

TECHNICAL FIELD OF THE INVENTION

The present invention relates to the use of Pyrrolopyrimidines, some of which are known, for controlling harmful plants and animals. Additionally, the invention also relates to novel pyrrolopyrimidines and to a process for their preparation.

BACKGROUND OF THE INVENTION

It is already known that certain pyrrolopyrimidines have pharmacological properties (cf. J. Med. Chem. 1995, (38), 3884–3888). However, a fungicidal or insecticidal activity of these compounds has hitherto not been described.

It has now been found that the pyrrolopyrimidines of the formula

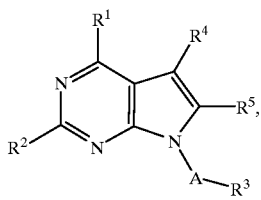

(I)

in which
- $R^1$ represents halogen, alkoxy or halogenoalkoxy,
- $R^2$ represents hydrogen, halogen, alkyl, halogenoalkyl, alkoxy, alkylthio, halogenoalkoxy or halogenoalkylthio,
- $R^3$ represents optionally substituted aryl or represents optionally substituted heteroaryl,
- $R^4$ and $R^5$ independently of one another each represent hydrogen, halogen or alkyl and
- A represents alkanediyl or represents an alkanedlyl which is interrupted by one or more heteroatoms or heteroatom groups, where the heteroatoms are not adjacent if a plurality of heteroatoms is present, and also their acid addition salts and metal salt complexes are highly suitable for controlling harmful plants and animals.

Surprisingly, the substances which can be used according to the invention have considerably better activity against harmful plants and animals than the constitutionally most similar compounds of the prior art having the same direction of action.

The formula (I) provides a general definition of the pyrrolopyrimidines which can be used according to the invention.

$R^1$ preferably represents fluorine, chlorine, bromine, iodine, alkoxy having 1 to 4 carbon atoms or halogenoalkoxy having 1 to 4 carbon atoms and 1 to 5 identical or different halogen atoms.

$R^2$ preferably represents hydrogen, fluorine, chlorine, bromine, iodine, alkyl having 1 to 4 carbon atoms, halogenoalkyl having 1 to 4 carbon atoms and 1 to 5 identical or different halogen atoms, alkoxy having 1 to 4 carbon atoms, alkylthio having 1 to 4 carbon atoms, halogenoalkoxy having 1 to 4 carbon atoms and 1 to 5 identical or different halogen atoms or halogenoalkylthio having 1 to 4 carbon atoms and 1 to 5 identical or different halogen atoms.

$R^3$ preferably represents aryl having 6 to 10 carbon atoms or represents heteroaryl having 3 to 12 ring members, where these radicals may in each case be mono- to pentasubstituted by identical or different substituents selected from the group consisting of halogen, cyano, nitro, formyl, carbamoyl, thiocarbamoyl;
alkyl, alkoxy, alkylthio, alkylsulphinyl or alkylsulphonyl having in each case 1 to 5 carbon atoms;
trialkylsilyl having 1 to 5 carbon atoms in each alkyl moiety;
alkenyl or alkenyloxy having in each case 2 to 4 carbon atoms;
halogenoalkyl, halogenoalkoxy, halogenoalkylthio, halogenoalkylsulphinyl or halogenoalkylsulphonyl having in each case 1 to 4 carbon atoms and 1 to 5 identical or different halogen atoms;
in each case straight-chain or branched halogenoalkenyl or halogenoalkenyloxy having in each case 2 to 4 carbon atoms and 1 to 5 identical or different halogen atoms;
alkylcarbonyl, alkylcarbonyloxy, alkoxycarbonyl, alkylsulphonyloxy, hydroxirninoalkyl, alkoximinoalkyl or cyanirmino(alkoxy)alkyl having in each case 1 to 4 carbon atoms in the individual alkyl moieties;
and in each case doubly attached dioxyalkylene having 1 or 2 carbon atoms or alkylene having 3 or 4 carbon atoms with which is optionally mono- to tetrasubstituted by identical or different substituents selected from the group consisting of halogen, alkyl having 1 to 4 carbon atoms and halogenoalkyl having 1 or 2 carbon atoms and 1 to 5 identical or different halogen atoms;
cycloalkyl having 3 to 6 carbon atoms;
a radical of the formula

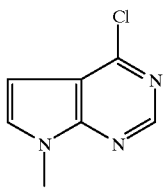

and also phenyl or phenoxy, where these two radicals may for their part be mono- to pentasubstituted by identical or different substituents selected from the group consisting of halogen, cyano, nitro, carbamoyl, thiocarbamoyl, alkyl having 1 to 5 carbon atoms, phenyl;
halogenoalkyl having 1 to 4 carbon atoms and 1 to 5 identical or different halogen atoms;
straight-chain or branched alkoxy or alkylthio having 1 to 4 carbon atoms;
and straight-chain or branched halogenoalkoxy or halogenoalkylthio having 1 to 4 carbon atoms and 1 to 5 identical or different halogen atoms;
and in each case doubly attached dioxyalkylene having 1 or 2 carbon atoms or alkylene having 3 to 4 carbon atoms which is optionally mono- to tetrasubstituted by identical or different substituents selected from the group consisting of halogen, alkyl having 1 to 4 carbon atoms and halogenoalkyl having 1 to 2 carbon atoms and 1 to 5 identical or different halogen atoms.

$R^4$ and $R^5$ independently of one another each preferably represent hydrogen, fluorine, chlorine, bromine, iodine or alkyl having 1 to 4 carbon atoms.

A preferably represents alkanediyl having 1 to 8 carbon atoms or represents alkanediyl having 1 to 8 chain members, where 1 or 2 (non-adjacent) chain members are replaced by oxygen, sulphur and/or $SO_2$ and where a termninal oxygen or sulphur atom or an $SO_2$ group is in each case attached to a radical $R^3$.

In the definitions, the saturated or unsaturated hydrocarbon chains, such as alkyl, alkanediyl, alkenyl or alkinyl, are in each case straight-chain or branched, including in combination with heteroatoms, such as an alkoxy, alkylthio or alkylamino.

$R^1$ particularly preferably represents fluorine, chlorine, bromine, methoxy, ethoxy, n- or i-propoxy, difluoromethoxy, trifluoromethoxy, difluorochloromethoxy, trifluoroethoxy.

$R^2$ particularly preferably represents hydrogen, fluorine, chlorine, bromine, methyl, ethyl, n- or i-propyl, n-, i-, s- or t-butyl, methoxy, ethoxy, n- or i-propoxy, methylthio, ethylthio, n- or i-propylthio, trifluoromethyl, trifluoroethyl, difluoromethoxy, trifluoromethoxy, difluorochloromethoxy, trifluoroethoxy, difluoromethylthio, difluorochloromethylthio, trifluoromethylthio or trifluoroethylthio.

$R^3$ particularly preferably represents phenyl, furyl, thienyl, thiazolyl, thiadiazolyl, pyridyl or pyrimidyl, where these radicals may be mono- to trisubstituted by identical or different substituents selected from the group consisting of fluorine, chlorine, bromine, cyano, nitro, formyl, methyl, ethyl, n- or i-propyl, n-, i-, s- or t-butyl, 1-, 2-, 3- or neo-pentyl, 1-, 2-, 3- or 4-(2-methylbutyl), methoxy, ethoxy, n- or i-propoxy, methylthio, ethylthio, n- or i-propylthio, methylsuiphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl, trifluoromethylsulphonyl, trimethylsilyl, acetyl, propionyl, acetyloxy, methoxycarbonyl, ethoxycarbonyl, butoxycarbonyl, methylsulphonyloxy, ethylsulphonyloxy, hydroximinomethyl, hydroximinoethyl, methoximinomethyl, ethoximinomethyl, methoximinoethyl, ethoximinoethyl or cyanoimino(methoxy)methyl, in each case doubly attached ethylenedioxy, methylenedioxy or trimethylene (propane-1,3-diyl), which is optionally mono- to tetrasubstituted by identical or different substituents selected from the group consisting of fluorine, chlorine, methyl, trifluoromethyl, ethyl, n- or i-propyl, cyclopropyl, cyclopentyl or cyclohexyl, a radical of the formula

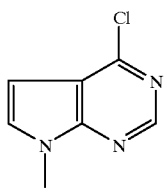

and also phenyl or phenoxy, where these two radicals may for their part be mono- to trisubstituted by identical or different substituents selected from the group consisting of fluorine, chlorine, bromine, cyano, nitro, formyl, methyl, ethyl, n- or i-propyl, n-, i-, s- or t-butyl, 1-, 2-, 3- or neo-pentyl, 1-, 2-, 3- or 4-(2-methylbutyl), methoxy, ethoxy, n- or i-propoxy, methylthio, ethylthio, n- or i-propylthio, trifluoromethyl, trifluoroethyl, difluoromethoxy, trifluoromethoxy, difluorochloromethoxy, trifluoroethoxy, difluoromethylthio, difluorochloromethylthio, trifluoromethylthio and phenyl, and in each case doubly attached ethylenedioxy, methylenedioxy or trimethylene (propane-1,3-diyl), which is optionally mono- to tetrasubstituted by identical or different substituents selected from the group consisting of fluorine, chlorine, methyl, trifluoromethyl, ethyl, n- or i-propyl.

$R^4$ and $R^5$ independently of one another each particularly preferably represent hydrogen, methyl, fluorine, chlorine, bromine or iodine.

A particularly preferably represents the groups —$CH_2$—

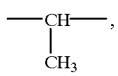

$CH_2$—$CH_2$—, 1,1-, 1,2-, 1,3- or 2,2-propylene, 1,1-, 1,2-, 1,3-, 1,4-, 2,2- or 2,3-butylene or 1,1-, 1,2- or 1,3-(2-methyl-propylene), —$(CH_2)_2$—O—, —$(CH_2)_2$—S—, —$(CH_2)_3$—O—, —$(CH_2)_3$—S—, —$(CH_2)_4$—O—, —$(CH_2)_4$—S—, —$(CH_2)_5$—O—, —$(CH_2)_5$—S—, —$(CH_2)_6$—O—, —$(CH_2)_6$—S—or —$(CH_2)_2$—$SO_2$—, where in each case the oxygen or the sulphur atom or the $SO_2$ group of the abovementioned groups is attached to the radical $R^3$.

Compounds which are preferably to be used according to the invention also include addition products of acids and those pyrrolopyrimidines of the formula (I) in which $R^1$, $R^2$, $R^3$, $R^4$, $R^5$ and A each have those meanings which have been mentioned as being preferred for these radicals.

The acids which can be added preferably include hydrohalic acids, such as, for example, hydrochloric acid and hydrobromic acid, in particular hydrochloric acid, furthermore phosphoric acid, sulphuric acid, nitric acid, mono- and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and also sulphonic acids, such as, for example, p-toluenesulphonic acid, 1,5-naphthalinedisulphonic acid, saccharine and thiosaccharine.

Preferred compounds according to the invention are additionally the addition products of salts of metals of main groups II to IV and sub-groups I and II and also IV to VIII of the Periodic Table of the Elements and those pyrrolopyrimidines of the formula (I) in which $R^1$, $R^2$, $R^3$, $R^4$, $R^5$ and A each have those meanings which have been mentioned as being preferred for these radicals.

Particular preference in this context is given to salts of copper, zinc, manganese, magnesium, tin, iron and nickel. Suitable anions of these salts are those which are derived from those acids which lead to physiologically acceptable addition products.

Particularly preferred acids of this kind in this context are the hydrohalic acids, such as, for example, hydrochloric acid and hydrobromic acid, furthermore phosphoric acid, nitric acid and sulphuric acid.

Some of the pyrrolopyrimidines which can be used according to the invention are known (cf. J. Med. Chem. 1995, (38), 3884–3888).

The pyrrolopyrimidines of the formula

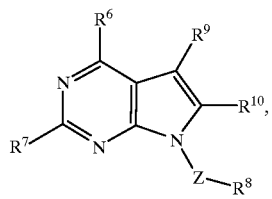

(Ia)

in which
a) $R^6$ represents fluorine, chlorine, bromine, methoxy, ethoxy, n- or i-propoxy, difluoromethoxy, trifluoromethoxy, difluorochloromethoxy, trifluoroethoxy, $R^7$ represents hydrogen, fluorine, chlorine, bromine, methyl, ethyl, n- or i-propyl, n-, i-, s- or t-butyl, methoxy, ethoxy, n- or i-propoxy, methylthio, ethylthio, n- or i-propylthio, trifluoromethyl, trifluoroethyl, difluoromethoxy, trifluoromethoxy, difluorochloromethoxy, trifluoroethoxy, difluoromethylthio, difluorochloromethylthio, trifluoromethylthio or trifluoroethylthio, $R^8$ represents phenyl, furyl, thienyl, thiazolyl, thiadiazolyl, pyridyl or pyrimidyl, where these radicals may be mono- to trisubstituted by identical or different substituents selected from the group consisting of fluorine, chlorine, bromine, cyano, nitro, formyl, methyl, ethyl, n- or i-propyl, n-, i-, s- or t-butyl, 1-, 2-, 3- or neo-pentyl, 1-, 2-, 3- or 4-(2-methylbutyl), methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl, trifluoromethylsulphonyl, trimethylsilyl, acetyl, propionyl, acetyloxy, methoxycarbonyl, ethoxycarbonyl, butoxycarbonyl, methylsulphonyloxy, ethylsulphonyloxy, hydroximinomethyl, hydroximinoethyl, methoximinomethyl, ethoximinomethyl, methoximinoethyl, ethoximinoethyl or cyanoimino(methoxy)methyl, in each case doubly attached ethylenedioxy, methylenedioxy or trimethylene (propane-1,3-diyl) which is optionally mono- to tetrasubstituted by identical or different substituents selected from the group consisting of fluorine, chlorine, methyl, trifluoromethyl, ethyl, n- or i-propyl, cyclopropyl, cyclopentyl or cyclohexyl, a radical of the formula

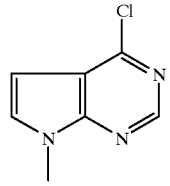

and also phenyl or phenoxy, where these two radicals may for their part be mono- to trisubstituted by identical or different substituents selected from the group consisting of fluorine, chlorine, bromine, cyano, nitro, formyl, methyl, ethyl, n- or i-propyl, n-, i-, s- or t-butyl, 1-, 2-, 3- or neo-pentyl, 1-, 2-, 3- or 4-(2-methylbutyl), methoxy, ethoxy, n- or i-propoxy, methylthio, ethylthio, n- or i-propylthio, trifluoromethyl, trifluoroethyl, difluoromethoxy, trifluoromethoxy, difluorochloromethoxy, trifluoroethoxy, difluoromethylthio, difluorochloromethylthio, trifluoromethylthio and phenyl, and in each case doubly attached ethylenedioxy, methylenedioxy or trimethylene (propane- 1,3-diyl), which is optionally mono- to tetrasubstituted by identical or different substituents selected from the group consisting of fluorine, chlorine, methyl, trifluoromethyl, ethyl, n- or i-propyl.

$R^9$ and $R^{10}$ independently of one another each represent hydrogen, methyl, fluorine, chlorine, bromine or iodine, Z represents the groups —$CH_2$—$CH_2$—, 1,1-, 1,2-, 1,3- or 2,2-propylene, 1,1-, 1,2-, 1,3-, 1,4-, 2,2-, 2,3-butylene or 1,1-, 1,2- or 1,3-(2-methylpropylene), —$(CH_2)_2$—O—, —$(CH_2)_2$—S—, —$(CH_2)_3$—O—, —$(CH_2)_3$—S—, —$(CH_2)_4$—O—, —$(CH_2)_4$—S—, —$(CH_2)_5$—O—, —$(CH_2)_5$—S—, —$(CH_2)_6$—O—, —$(CH_2)_6$—S— or —$(CH_2)_2$—$SO_2$—, where in each case the oxygen or the sulphur atom or the $SO_2$ group of the abovementioned groups is attached to the radical $R^8$, or b) $R^6$ represents fluorine, chlorine, bromine, methoxy, ethoxy, n- or i-propoxy, difluoromethoxy, trifluoromethoxy, difluoromethoxy, trifluoromethoxy, $R^7$ represents hydrogen, fluorine, chlorine, bromine, methyl, ethyl, n- or i-propyl, n-, i-, s- or t-butyl, methoxy, ethoxy, n- or i-propoxy, methylthio, ethylthio, n- or i-propylthio, trifluoromethyl, trifluoroethyl, difluoromethoxy, trifluoromethoxy, difluorochloromethoxy, trifluoroethoxy, difluoromethylthio, difluorochloromethylthio, trifluoromethylthio or trifluoroethylthio, $R^8$ represents phenyl which is mono- to trisubstituted by identical or different substituents selected from the group consisting of bromine, cyano, nitro, formyl, methyl, ethyl, n- or i-propyl, n-, i-, s- or t-butyl, 1-, 2-, 3- or neo-pentyl, 1-, 2-, 3- or 4-(2-methylbutyl), methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, tifluoroethoxy, difluoromethylthio, difluorochloromethylthio, trifluoromethylthio, trifluoromethylsulphinyl, trifluoromethylsulphonyl, trimethylsilyl, acetyl, propionyl, acetyloxy, methoxycarbonyl, ethoxycarbonyl, butoxycarbonyl, methylsulphonyloxy, ethylsulphonyloxy, hydroxirninomethyl, hydroxiniinoethyl, methoximinomethyl, ethoximinomethyl, methoximinoethyl, ethoximinoethyl or cyanoimino(methoxy)methyl, respectively doubly attached ethylenedioxy, methylenedioxy or trimethylene (propane-1,3-diyl), which is optionally mono- to tetrasubstituted by identical or different substituents selected from the group consisting of fluorine, chlorine, methyl, trifluoromethyl, ethyl, n- or i-propyl,
cyclopropyl, cyclopentyl or cyclohexyl,
and also phenyl or phenoxy, where these two radicals may for their part be mono- to trisubstituted by identical or different substituents selected from the group consisting of fluorine, chlorine, bromine, cyano, nitro, formyl, methyl, ethyl, n- or i-propyl, n-, i-, s- or t-butyl, 1-, 2-, 3- or neo-pentyl, 1-, 2-, 3- or 4-(2-methylbutyl), methoxy, ethoxy, n- or i-propoxy, methylthio, ethylthio, n- or i-propylthio, trifluoromethyl, trifluoroethyl, difluoromethoxy, trifluoromethoxy, difluorochloromethoxy, trifluoroethoxy, difluoromethylthio, difluorochloromethylthio, trifluoromethylthio and phenyl,
and in each case doubly attached ethylenedioxy, methylenedioxy or trimethylene (propane-1,3-diyl), which is optionally mono- to tetrasubstituted by identical or different substituents selected from the group consisting of fluorine, chlorine, methyl, trifluoromethyl, ethyl, n- or i-propyl, or $R^8$ represents thienyl or furyl, where these radials are mono- to trisubstituted by identical or different substituents selected from the group consisting of fluorine, chlorine, bromine, cyano, nitro, fornyl, methyl, ethyl, n- or i-propyl, n-, i-, s- or t-butyl, 1-, 2-, 3- or neo-pentyl, 1-, 2-, 3- or 4-(2-methylbutyl), methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl, trifluoromethylsulphonyl, trimethylsilyl, acetyl, propionyl, acetyloxy, methoxycarbonyl, ethoxycarbonyl, butoxycarbonyl, methylsulphonyloxy, ethylsulphonyloxy, hydroximinomethyl, hydroximinoethyl, methoximinomethyl, ethoximinomethyl, methoximinoethyl, ethoximinoethyl . or cyanoimino (methoxy)methyl,
in each case doubly attached ethylenedioxy, methylenedioxy or trimethylene (propane-1,3-diyl), which is optionally mono- to tetrasubstituted by identical or different substituents selected from the group consisting of fluorine, chlorine, methyl, trifluoromethyl, ethyl, n- or i-propyl,
cyclopropyl, cyclopentyl or cyclohexyl,
and also phenyl or phenoxy, where these two radicals may for their part be mono- to trisubstituted by identical or different substituents selected from the group consisting of fluorine, chlorine, bromine, cyano, nitro, formyl, methyl, ethyl, n- or i-propyl, n-, i-, s- or t-butyl, 1-, 2-, 3- or neo-pentyl, 1-, 2-, 3- or 4-(2-methylbutyl), methoxy, ethoxy, n- or i-propoxy, methylthio, ethylthio, n- or i-propylthio, trifluoromethyl, trifluoroethyl, difluoromethoxy, trifluoromethoxy, difluorochloromethoxy, trifluoroethoxy, difluoromethylthio, difluorochloromethylthio, trifluoromethylthio and phenyl,
and in each case doubly attached ethylenedioxy, methylenedioxy or trimethylene (propane-1,3-diyl), which is mono- to tetrasubstituted by identical or different substituents selected from the group consisting of fluorine, chlorine, methyl, trifluoromethyl, ethyl, n- or i-propyl, or $R^8$ represents thiazolyl, thiadiazolyl, pyridyl or pyrimridyl where these radicals may be mono- to trisubstituted by identical or different substituents selected from the group consisting of fluorine, chlorine, bromine, cyano, nitro, formyl, methyl, ethyl, n- or i-propyl, n-, i-, s- or t-butyl, 1-, 2-, 3- or neo-pentyl, 1-, 2-, 3- or 4-(2-methylbutyl), methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl, trifluoromethylsulphonyl, trimethylsilyl, acetyl, propionyl, acetyloxy, methoxycarbonyl, ethoxycarbonyl, butoxycarbonyl, methylsulphonyloxy, ethylsulphonyloxy, hydroximinomethyl, hydroximinoethyl, methoximinomethyl, ethoximinomethyl, methoximinoethyl, ethoximinoethyl or cyanoimino (methoxy)methyl,
in each case doubly attached ethylenedioxy, methylenedioxy or trimethylene (propane-1,3-diyl) which is optionally mono- to tetrasubstituted by identical or different substituents selected from the group consisting of fluorine, chlorine, methyl, trifluoromethyl, ethyl, n- or i-propyl,
cyclopropyl, cyclopentyl or cyclohexyl,
a radical of the formula

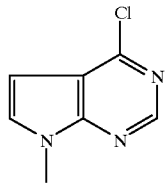

and also phenyl or phenoxy, where these two radicals may for their part be mono- to trisubstituted by identical or different substituents selected from the group consisting of fluorine, chlorine, bromine, cyano, nitro, formyl, methyl, ethyl, n- or i-propyl, n-, i-, s- or t-butyl, 1-, 2-, 3- or neo-pentyl, 1-, 2-, 3- or 4-(2-methylbutyl), methoxy, ethoxy, n- or i-propoxy, methylthio, ethylthio, n- or i-propylthio, trifluoromethyl, trifluoroethyl, difluoromethoxy, trifluoromethoxy, difluorochloromethoxy, trifluoroethoxy, difluoromethylthio, difluorochloromethylthio, trifluoromethylthio and phenyl,
and in each case doubly attached ethylenedioxy, methylenedioxy or trimethylene (propane-1,3-diyl), which is optionally mono to tetrasubstituted by identical or different substituents selected from the group consisting of fluorine, chlorine, methyl, trifluoromethyl, ethyl, n- or i-propyl,
$R^9$ and $R^{10}$ independently of one another each represent hydrogen, methyl, fluorine, chlorine, bromine or iodine and Z represents the groups —CH$_2$— or

—CH—
|
CH$_3$ or c) R$^6$ represents fluorine, chlorine, bromine, methoxy, ethoxy, n- or i-propoxy, difluoromethoxy, trifluoromethoxy, difluoromethoxy, trifluoromethoxy, R$^7$ represents hydrogen, fluorine, chlorine, bromine, methyl, ethyl, n- or i-propyl, n-, i-, s- or t-butyl, methoxy, ethoxy, n- or i-propoxy, methylthio, ethylthio, n- or i-propylthio, trifluoromethyl, trifluoroethyl, difluoromethoxy, trifluoromethoxy, difluorochloromethoxy, trifluoroethoxy, difluoromethylthio, difluorochloromethylthio, trifluoromethylthio or trifluoroethylthio, R$^8$ represents phenyl which is optionally mono- to trisubstituted by identical or different substituents selected from the group consisting of fluorine, chlorine and methoxy, R$^9$ represents hydrogen, fluorine, chlorine, bronine or iodine, R$^{10}$ represents hydrogen, fluorine, chlorine, bromine or iodine and Z represents the groups —CH$_2$— or

—CH—
|
CH$_3$ but where R$^9$ and R$^{10}$ do not simultaneously represent hydrogen if R$^8$ represents phenyl or 2-fluorophenyl and Z represents —CH$_2$—, and their acid addition salts and metal salt complexes are novel.

The pyrrolopyrimidines of the formula (Ia) and their acid addition salts and metal salt complexes can be prepared by reacting pyrrolopyrimidine derivatives of the formula (II)

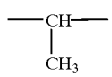

in which

R$^6$, R$^7$, R$^9$, and R$^{10}$ are each as defined above with compounds of the formula

X—Z—R$^8$ (III), in which

Z and R$^8$ are each as defined above and

X represents halogen, alkylsulphonyl or arylsulphonyl, if appropriate in the presence of an acid binder and if appropriate in the presence of a diluent, and subsequently adding, if appropriate, an acid or a metal salt.

The other compounds of the formula (I) can be prepared in the same manner.

A large number of the compounds which can be used according to the invention contain asynrmnetrically substituted carbon atoms. These compounds may be present in the form of stereoisomers or as mixtures thereof. The invention relates both to the individual isomers and to their mixtures. Using 4-chloro-2-methyl-7H-pyrrolo[2,3-d]pyrimidine and benzyl chloride as starting materials, the course of the process according to the invention can be illustrated by the following equation:

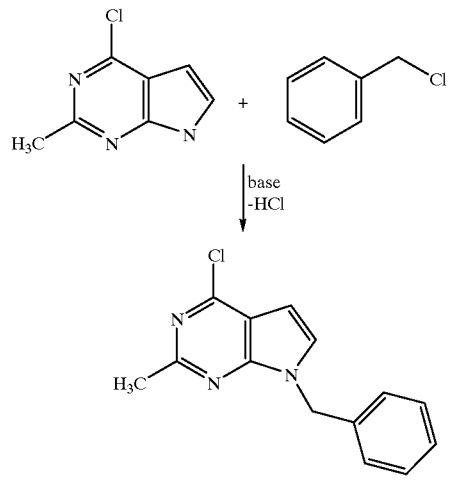

The formula (II) provides a general definition of the pyrrolopyrimidine derivatives required as starting materials for carrying out the process according to the invention. In this formula (II), R$^6$, R$^7$, R$^9$ and R$^{10}$ each have those meanings which have already been mentioned in connection with the description of the compounds of the formula (Ia) according to the invention as being preferred or as being particularly preferred for R$^6$, R$^7$, R$^9$ and R$^{10}$.

The starting materials of the formula (II) are known or can be prepared by known processes (cf. Chem.Ber., (1942), 75, 755; J.Org.Chem., (1961) 26, 3809; Chem.Ber. (1979) 112, 3432; Chem.Ber. (1979) 112, 799; Liebigs Ann.Chem. (1984), 273–282; Liebigs Ann.Chem. (1984) 722–733; Liebigs Ann.Chem. (1985) 312–320 J.Med.Chem. (1985) 28, 1461–1467).

The formula (III) provides a general definition of the substances required as reaction components for carrying out the process according to the invention. In this formula, R$^8$ and Z each have those meanings which have already been mentioned in connection with the description of the compounds of the formula (Ia) according to the invention. X preferably represents chlorine, bromine, methylsulphonyl or 4-tolylsulphonyl.

The compounds of the formula (III) are known or can be prepared by known processes.

Suitable acid binders for carrying out the process according to the invention are all customary inorganic or organic bases. Preference is given to using alkaline earth metal or alkali metal hydrides, hydroxides, amides, alkoxides, acetates, carbonates or bicarbonates, such as sodium hydride, sodium amide, sodium methoxide, sodium ethoxide, potassium tert-butoxide, sodium hydroxide, potassium hydroxide, sodium acetate, potassium acetate, calcium acetate, sodium carbonate, potassium carbonate, potassium bicarbonate or sodium bicarbonate, furthermore ammonium compounds, such as ammonium hydroxide, ammonium acetate or ammonium carbonate, and also tertiary amines, such as trimethylamine, triethylamine or tributylaamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

Suitable diluents for carrying out the process according to the invention are all customary inert organic solvents. Preference is given to using aliphatic, alicyclic or aromatic hydrocarbons, such as petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisol; ketones, such as acetone, butanone, methylisobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters such as methyl acetate or ethyl acetate; sulphoxides, such as dimethyl sulphoxide; sulphones, such as sulpholane.

When carrying out the process according to the invention, the reaction temperatures can be varied within a relatively wide range. In general, the reaction is carried out at temperatures between −20° C. and +180° C., preferably at temperatures between 20° C. and 130° C.

The process according to the invention is usually carried out under atmospheric pressure. However, it is also possible to carry out the process according to the invention under elevated or reduced pressure.

When carrying out the process according to the invention, generally 0.5 to 10 mol, preferably 0.8 to 3 mol, of a compound of the formula (III) are employed per mole of pyrrolopyrimidine derivative of the formula (II). Work-up is carried out by customary methods. In general, the reaction mixture is concentrated under reduced pressure, the residue that remains is taken up in an organic solvent which is only sparingly miscible with water, and the resulting solution is washed with water and, after drying, concentrated under reduced pressure. The product that is obtained can, if appropriate, be freed of any impurities that may still be present using customary methods, for example chromatography or recrystallization.

The pyrrolopyrimidines of the formula (Ia) can be converted into acid addition salts or metal salt complexes.

For preparing acid addition salts of the compounds of the formula (Ia), preference is given to using those acids which have already been mentioned as being preferred acids in connection with the description of the acid addition salts which can be used according to the invention.

The acid addition salts of the compounds of the formula (Ia) can be obtained in a simple manner by customary salt formation methods, for example by dissolving a compound of the formula (Ia) in a suitable inert solvent and addition of the acid, for example hydrochloric acid, and can be purified in a known manner, for example by filtering off, isolation and, if appropriate, by washing with an inert organic solvent.

For preparing metal salt complexes of the compounds of the formula (Ia), preference is given to using those salts of metals which have already been mentioned in connection with the description of the metal salt complexes which can be used according to the invention as preferred metal salts.

The metal salt complexes of the compounds of the formula (Ia) can be obtained in a simple manner by customary processes, for example by dissolving the metal salt in alcohol, for example ethanol, and adding it to compounds of the formula (Ia). Metal salt complexes can be purified in the known manner, for example by filtering off, isolation and, if appropriate, by recrystallization.

The active compounds which can be used according to the invention have a potent microbicidal activity and can be employed for controlling undesirable microorganisms, such as fungi and bacteria, in crop protection and in the protection of materials.

Fungicides can be employed in crop protection for controlling Plasmo-diophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceac and Streptomycetaceae.

Some pathogens causing fungal and bacterial diseases which come under the generic names listed above are mentioned as examples, but not by way of limitation:

Xanthomonas species, such as *Xanthomonas campestris* pv. *oryzae;*

Pseudomonas species, such as *Pseudomonas syringae* pv. *lachrymans;*

Erwinia species, such as *Erwinia amylovora;*

Pythium species, such as *Pythium ultimum;*

Phytophthora species, such as *Phytophthora infestans;*

Pseudoperonospora species, such as *Pseudoperonospora humuli* or *Pseudoperonospora cubensis;*

Plasmopara species, such as *Plasmopara viticola;*

Bremnia species, such as *Bremia lactucae,*

Peronospora species, such as *Peronospora pisi* or *P. brassicae;*

Erysiphe species, such as *Erysiphe graminis;*

Sphaerotheca species, such as *Sphaerotheca fuliginea;*

Podosphaera species, such as for example *Podosphaera leucotricha;*

Venturia species, such as *Venturia inaequalis;*

Pyrenophora species, such as *Pyrenophora teres* or *P. graminea* (conidia form: Drechslera, syn: Helminthosporium);

Cochliobolus species, such as *Cochliobolus sativus* (conidia form: Drechslera, syn: Helminthosporium);

Uromyces species, such as *Uromyces appendiculatus;*

Puccinia species, such as *Puccinia recondita;*

Sclerotinia species, such as *Sclerotinia sclerotiorum;*

Tilletia species, such as *Tilletia caries;*

Ustilago species, such as *Ustilago nuda* or *Ustilago avenae;*

Pellicularia species, such as *Pellicularia sasakii;*

Pyricularia species, such as *Pyricularia oryzae;*

Fusarium species, such as *Fusarium culmorum;*

Botrytis species, such as *Botrytis cinerea;*

Septoria species, such as *Septoria nodorum;*

Leptosphaeria species, such as *Leptosphaeria nodorum;*

Cercospora species, such as *Cercospora canescens;*

Alternaria species, such as for example *Alternaria brassicae;*

Pseudocercosporella species, such as *Pseudocercosporella herpotrichoides.*

The fact that the active compounds are well tolerated by plants at the concentrations required for controlling plant diseases permits the treatment of aerial parts of plants, of propagation stock and seeds, and of the soil.

The active compounds which can be used according to the invention can be employed here particularly successfully for controlling cereal diseases, such as against Leptospaeria species, diseases in viticulture, food and vegetable growing, such as against Venturia, Podosphaera and Plasmopara species.

Other cereal diseases, such as Erysiphe, Septoria, Pyrenophora or Cochliobolus species, and also rice diseases, such as Pyricularia species, are also controlled very successfully.

In the protection of materials, the substances which can be used according to the invention can be employed for protecting industrial materials against attack and destruction by undesirable microorganisms.

In the present context, the term industrial materials refers to non-living materials which have been prepared for use in industry. Examples are industrial materials which are to be protected by active compounds according to the invention against microbial alteration or destruction, adhesives, sizes, paper and card, textiles, leather, wood, coating compositions and plastic articles, cooling lubricants and other materials which can be infested or decomposed by microorganisms. In the context of the materials to be protected mention may also be made of parts of production plants, for example cooling water circuits, which may be adversely affected by reproduction of microorganisms. Preferred industrial materials of which mention may be made in the context of the present invention are adhesives, sizes, papers and cards, leather, wood, coating compositions, cooling lubricants and heat transfer fluids, particularly preferably wood.

By way of example, mention may be made of microorganisms of the following genera:
Alternaria, such as *Alternaria tenuis*,
Aspergillus, such as *Aspergillus niger*,
Chaetomium, such as *Chaetomium globosum*,
Coniophora, such as *Coniophora puetana*,
Lentinus, such as *Lentinus tigrinus*,
Penicillium, such as *Penicillium versicolor*,
Aureobasidium, such as *Aureobasidium pullulans*,
Sclerophoma, such as *Sclerophoma pityophila*,
Trichoderma, such as *Trichoderma viride*,
Escherichia, such as *Escherichia coli*,
Pseudomonas, such as *Pseudomonas aeruginosa*,
Staphylococcus, such as *Staphylococcus aureus*.

The active compounds which can be used according to the invention are well tolerated by plants and have favourable homeotherm toxicity, and they can additionally be employed for controlling animal pests, in particular insects, arachnids and nematodes, which are encountered in agriculture, in forests, in horticulture, in the protection of stored products and of materials and also in the hygiene sector and in the veterinary field. The substances are active against normally sensitive and resistant species and also against pests in all or specific stages of development. The abovementioned animal pests include:

From the order of the Isopoda, for example, *Oniscus asellus, Armadillidium vulgare* and *Porcellio scaber*.

From the order of the Diplopoda, for example, *Blaniulus guttulatus*. From the order of the Chilopoda, for example, *Geophilus carpophagus* and *Scutigera spec.*

From the order of the Symphyla, for example, *Scutigerella immaculata*.

From the order of the Thysanura, for example, *Lepisma saccharina*.

From the order of the Collembola, for example, *Onychiurus armatus*.

From the order of the Orthoptera, for example, *Blatta orientalis, Periplaneta americana, Leucophaea maderae, Blattella germanica, Acheta domesticus, Gryllotalpa spp., Locusta migratoria migratorioides, Melanoplus differentialis* and *Schistocerca gregaria*.

From the order of the Dermaptera, for example, *Forficula auricularia*.

From the order of the Isoptera, for example, Reticulitermes spp.

From the order of the Anoplura, for example, *Pediculus humanus corporis*, Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci*.

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix*, Pemphigus spp., *Macrosiphum avenae*, Myzus spp., *Phorodon humuli, Rhopalosiphum padi*, Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and *Psylla spp.*

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., *Spodoptera exigua, Mamestra brassicae, Panolis flammea, Spodoptera litura*, Spodoptera spp., *Trichoplusia ni, Carpocapsa pomonella*, Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae*, Diabrotica spp., *Psylliodes chrysocephala, Epilachna varivestis*, Atomaria spp., *Oryzaephilus surinamensis*, Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis* and *Costelytra zealandica*.

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp.

From the order of the Arachnida, for example, *Scorpio maurus* and *Latrodectus mactans*.

From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The phytoparasitic nematodes include Pratylenchus spp., *Radopholus sirmilis, Ditylenchus dipsaci, Tylenchulus semipenetrans*, Heterodera spp., Globodera spp., Meloidogyne spp., Aphelenchoides spp., Longidorus spp., Xiphinema spp. and Trichodorus spp.

The substances which can be used according to the invention can be employed particularly successfully for controlling plant-damaging mites, such as against the greenhouse red spider mite (*Tetranychus urticae*), or for controlling plant-damaging insects, such as against the caterpillars of the diamond-back moth (*Plutella maculipennis*), the larvae of the mustard beetle (*Phaedon cochleariae*) and also the green rice leaf hopper (*Nephotettix cincticeps*).

The substances which can be used according to the invention are not only active against plant, hygiene and stored-product pests, but also, in the veterinary medicine sector, against animal parasites (ectoparasites) such as hard ticks, soft ticks, mange mites, Trombiidae, flies (stinging and sucking), parasitic fly larvae, lice, hair lice, bird lice and fleas. These parasites include:

From the order of the Anoplurida, for example, Haematopinus spp., Linognathus spp., Pediculus spp., Phtirus spp. and Solenopotes spp.

From the order of the Mallophagida and the sub-orders Amblycerina and Ischnocerina, for example, Trimenopon spp., Menopon spp., Trinoton spp., Bovicola spp., Werneckiella spp., Lepikentron spp., Damalina spp., Trichodectes spp. and Felicola spp.

From the order of the Diptera and the sub-orders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp and Melophagus spp.

From the order of the Siphonapterida, for example, Pulex spp., Ctenocephalides spp., Xenopsylla spp. and Ceratophyllus spp.

From the order of the Heteropterida, for example, Cimex spp., Triatoma spp., Rhodnius spp. and Panstrongylus spp.

From the order of the Blattarida, for example, *Blatta orientalis, Periplaneta americana, Blattela germanica* and supella spp.

From the sub-class of the Acaria (Acarida) and the orders of the Meta- and Mesostigmata, for example, Argas spp., Ornithodorus spp., Otabius spp., Ixodes spp., Amblyomma spp., Boophilus spp., Dermacentor spp., Haemaphysalis spp., Hyalomma spp., Rhipicephalus spp., Dermanyssus spp., Raillietia spp., Pneumonyssus spp., Sternostoma spp. and Varroa spp.

From the order of the Actinedida (Prostigmata) and Acaridida (Astigmata), for example, Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knernidocoptes spp., Cytodites spp. and Larninosioptes spp.

The active compounds which can be used according to the invention are also suitable for controlling arthropods which attack agricultural livestock, such as, for example, cattle, sheep, goats, horses, pigs, donkeys, camels, buffalo, rabbits, chickens, turkeys, ducks, geese, honeybees, other domestic animals such as, for example dogs, cats, cage birds, aquarium fish, and so-called experimental animals, such as, for example, hamsters, guinea pigs, rats and mice. By controlling these arthropods, it is intended to reduce deaths and decreasing performance (in meat, milk, wool, hides, eggs, honey and the like), so that more economical and simpler animal keeping is possible by using the active compounds according to the invention.

Furthermore, it has been found that the compounds which can be used according to the invention have a potent insecticidal action against insects which destroy industrial materials.

The following insects may be mentioned by way of example and as being preferred, but without any limitation:

Beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis*; Xyleborus spec., Tryptodendron spec., *Apate monachus, Bostrychus capucins, Heterobostrychus brunneus*, Sinoxylon spec., *Dinoderus minutus*

Dermapterans, such as *Sirexjuvencus, Urocerus gigas, Urocerus gigas taignus, Urocerus augur*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails, such as *Lepisma saccharina*.

Industrial materials are to be understood as meaning, in the present context, non-live materials, such as, preferably, synthetic materials, glues, sizes, paper and board, leather, wood and timber products, and paint.

The materials to be very particularly preferably protected against attack by insects are wood and timber products.

Wood and timber products which can be protected by compounds according to the invention are to be understood as meaning, for example, construction timber, wooden beams, railway sleepers, bridge components, jetties, wooden vehicles, boxes, pallets, containers, telephone poles, wood lagging, windows and doors made of wood, plywood, particle board, joiner's articles, or wood products which, quite generally, are used in the construction of houses or in joinery.

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. In the case of the use of water as an extender, organic solvents can, for example, also be used as auxiliary solvents. Essentially, the following are suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds which can be used according to the invention can be used as such or in their formulations also mixed with known fungicides, bactericides, acaricides, nematicides or insecticides in order thus, for example, to widen the spectrum of action or to prevent development of resistance. In many cases, synergistic effects are achieved, i.e. the activity of the mixture exceeds the activity of the individual components.

Examples of co-components in mixtures are the following compounds:

Fungicides:
aldimorph, ampropylfos, ampropylfos potassium, andoprim, anilazine, azaconazole, azoxystrobin,
benalaxyl, benodanil, benomyl, benzamacril, benzamacril-isobutyl, bialaphos, binapacryl, biphenyl, bitertanol, blasticdiin-S, bromuconazole, bupirimate, buthiobate,
calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram,
debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon,
edifenphos, epoxiconazole, etaconazole, ethirimol, etridiazole,
famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimnidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox,
guazatine,
hexachlorobenzene, hexaconazole, hymexazole,
imazalil, imibenconazole, iminoctadine, iminoctadine albesilate, iminoctadine triacetate, iodocarb, ipconazole, iprobenfos (IBP), iprodione, irumamycin, isoprothiolane, isovaledione,
kasugamycin, kresoxim-methyl, copper preparations, such as: copper hydroxide, copper naphthenate, copper oxychloride, copper sulphate, copper oxide, oxine-copper and Bordeaux mixture,
mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin,
nickel dimethyldithiocarbamate, nitrothal-isopropyl, nuarimol,
ofurace, oxadixyl, oxamocarb, oxolinic acid, oxycarboxim, oxyfenthiin,
paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur,
quinconazole, quintozene (PCNB),
sulphur and sulphur preparations,
tebuconazole, tecloftalam, tecnazene, tetcyclasis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole,
uniconazole,
validamycin A, vinclozolin, viniconazole,
zarilamide, zineb, ziram and also
Dagger G,
OK-8705,
OK-8801,
2',6'-dibromo-2-methyl4'-trifluoromethoxy-4'-trifluoromethyl-1,3-thiazole-5-carboxanilide,
2,6-dichloro-N-(4-trifluoromethylbenzyl)-benzamnide,
2-aminobutane,
2-phenylphenol (OPP),
8-hydroxyquinoline sulphate,
cis-1-(4-chlorophenyl)-2-(1 H-1,2,4-triazol-1-yl)-cycloheptanol,
(5RS,6RS)-6-hydroxy-2,2,7,7-tetrarnethyl-5-(1H-1,2,4-triazol-1-yl)-3-octanone,
α-(2,4-dichlorophenyl)-β-methoxy-α-methyl-1H-1,2,4-triazole-1-ethanol,
α(1,1-dimethylethyl)-β-(2-phenoxyethyl)-1H-1,2,4-triazole-1-ethanol,
1-[1-[2-[(2 ,4-dichlorophenyl)-methoxy]-phenyl]-ethenyl]-1H-irnidazole,
bis-(1-methylethyl)-3-methyl4-[(3-methylbenzoyl)oxy]-2,5-thiophenedicarboxylate,
2,6-dichloro-N-[[4-(trifluoromethyl)-phenyl]-methyl]-benzamide,
(E)-α-(methoxyimino)-N-methyl-2-phenoxy-phenylacetamide, 9H-xanthene-2-[(phenylamino)-carbonyl]-9-carboxylic hydrazide,
O-methyl S-phenyl phenylpropylphosphoramidothioate,
N-(5-chloro-2-methylphenyl)-2-methoxy-N-(2-oxo-3-oxazolidinyl)-acetamide,
1-(2,4-dichlorophenyl)-2-(1H-1,2,4-triazol-1-yl)ethanone-O-(phenylmethyl)-oxime,
N-(2,6-dimethylphenyl)-2-methoxy-N-(tetrahydro-2-oxo-3-thienyl)-acetamide,
cis-4-[3-[4-(1,1-dimethylpropyl)-phenyl-2-methylpropyl]-2,6-dimethyl-morpholine hydrochloride,
1-(3,5-dichlorophenyl)-3-(2-propenyl)-2,5-pyrrolidindione,
1-methyl-5-nonyl-2-(phenylmethyl)-3-pyrrolidinole,
1-[[2-(4-chlorophenyl)-3-phenyloxiranyl]-methyl]- H-1,2,4-triazole, methanetetrathiol-sodium salt,
2-(2,3,3-triiodo-2-propenyl)-2H-tetrazole,
N-[3-chloro-4,5-bis(2-propinyloxy)-phenyl]-N'-methoxy-methanirnidamide,
α-(5-methyl-1,3-dioxan-5-yl)-β-[[4-(trifluoromethyl)-phenyl]-methylenel-1H-1,2,4-triazole-1-ethanol,
1-(2-methyl-1-naphthalenyl)-1H-pyrrol-2,5-dione,
N-(2,6-dimethylphenyl)-2-methoxy-N-(tetrahydro-2-oxo-3-furanyl)-acetamide,
3,4-dichloro-1-[4-(difluoromethoxy)-phenyl-1H-pyrrol-2,5-dione,
N-[2,2,2-trichloro-1-[(chloroacetyl)-amino]-ethyl]-benzamide,
N-formyl-N-hydroxy-DL-alanine-sodium salt,
N-(4-cyclohexylphenyl)-1,4,5,6-tetrahydro-2-pyrimidinamine,
4-methyl-tetrazolo[1,5-a]quinazolin-5(4H)-one,
2-chloro-N-(2,6-dimethylphenyl)-N-(isothiocyanatomethyl)-acetamide, ethyl [(4-chlorophenyl)-azo]-cyanoacetate,
N-(4-hexylphenyl)-1,4,5,6-tetrahydro-2-pyrimidinamine,
N-(2-chloro-4-nitrophenyl)-4-methyl-3-nitro-benzenesulphonarnide, methyl N-(chloroacetyl)-N-(2,6-dimethylphenyl)-DL-alaninate,
3-[2-(4-chlorophenyl)-5-ethoxy-3-isoxazolidinyl]-pyridine,
2-[(1-methylethyl)sulphonyl]-5-(trichloromethyl)-1,3,4-thiadiazole, spiro[2H]-1-benzopyrane-2,1'(3'H)-isobenzofuran]-3'-one,
methyl N-(2,6-dimethylphenyl)-N-(5-isoxazolylcarbonyl)-DL-alaninate, potassium bicarbonate,
1-[[2-(2,4-dichlorophenyl)-1,3-dioxolan-2-yl]-methyl]-1H-imidazole,
1-[(diiodomethyl)-sulphonyl]4-methyl-benzene,
2-bromo-2-(bromomethyl)-pentanedinitrile,
2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile, methyl 1-(2,3-dihydro-2,2-dimethyl-1H-inden-1-yl)-1H-imidazole-5-carboxylate,
2-chloro-N-(2,3-dihydro-1,1,3-trimethyl-1H-inden4-yl)-3-pyridinecarboxamide,
O,O-diethyl [2-(dipropylamino)-2-oxoethyl]-ethylphosphoramidothioate,
α-(2,4-dichlorophenyl)-β-fluoro-β-propyl-1H-1,2,4-triazole-1-ethanol,
3-(1,1-dimethylpropyl-1-oxo-1H-indene-2-carbonitrile,
2,6-dichloro-5-(methylthio)-4-pyrimidinyl-thiocyanate,
S-methyl 1,2,3-benzothiadiazole-7-carbothioate,
N-(6-methoxy)-3-pyridinyl)-cyclopropanecarboxamide,
3,5-dichloro-N-fcyano-[(1-methyl-2-propynyl)-oxy]-methyl]-benzamide,
4-chloro-2-cyano-N,N-dimethyl-5-(4-methylphenyl)-1H-imidazole-1-sulphonamide,
8-(1,1-dimethylethyl)-N-ethyl-N-propyl-1,4-dioxaspiro[4.5]decane-2-methanamine,
2,2-dichloro-N-[1-(4-chlorophenyl)-ethyl]-1-ethyl-3-methylcyclopropanecarboxamide,
N-(2,3-dichloro-4-hydroxyphenyl)-1-methyl-cyclohexanecarboxamide.

Bactericides:
bronopol, dichlorophen, nitrapyrin, nickel dimethyldithiocarbamate, kasugamnycin, octhilinone, furancarboxylic acid, oxytetracyclin, probenazole, streptomycin, tecloftalarn, copper sulphate and other copper preparations.

Insecticides/Acaricides/Nematicides:
abamnectin, AC 303 630, acephate, acrinathrin, alanycarb, aldicarb, alphamnethrin, armitraz, averrnec tin, AZ 60541, azadirachtin, azinphos A, azinphos M, azocyclotin, Bacillus thuringiensis, bendiocarb, benfuracarb, bensultap, betacyfluthrin, bifenthrin, BPMC, brofenprox, bromophos A, bufencarb, buprofezin, butocarboxim, butylpyridaben, cadusafos, carbaryl, carbofuran, carbophenothion, carbosulphan, cartap, CGA 157 419, CGA 184699, chloethocarb, chiorethoxyfos, chlorfenvinphos, chiorfluazuron, chiormephos, chiorpyrifos, chiorpyrifos M, cis-resmethrin, clocythrin, clofentezine, cyanophos, cycloprothrin, cyfluthrin, cyhalothrin, cyhexatin, cyperrnethrin, cyromazine, deltamethrin, demeton M, demeton S, demeton S-methyl, diafenthiuron, diazinon, dichlofenthion, dichiorvos, dicliphos, dicrotophos, diethion, diflubenzuron, dimethoate, dimethylvinphos, dioxathion, disuiphoton, edifenphos, emamectin, esfenvalerate, ethiofencarb, ethion, ethofenprox, ethoprophos, etrimphos, fenamniphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucytlirinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mevinphos, mesulphenphos, metaldehyde, methacrifos, metharnidophos, methidathion, methiocarb, methomyl, metolcarb, milbemectin, monocrotophos, moxidectin, naled, NC 184, MI 25, nitenpyram, omethoate, oxamyl, oxydemethon M, oxydeprofos, parathion A, parathion M, permethrin, phenthoate, phorate, phosalone, phosmet, phosphamidon, phoxim, pirinricarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos,

RH 5992, salithion, sebufos, silafluofen, sulphotep, sulprofos, tebufenozide, tebufenpyrad, tebupirimphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacrb, vamidothion, XMC, xylylcarb, zetamethrin.

It is also possible to admix other known active compounds, such as herbicides or fertilizers and growth regulators.

The active compounds can be used as such, in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by pouring, spraying, atonizing, broadcasting, dusting, foaming, brushing-on and the like. It is further possible to apply the active compounds by the ultra-low volume method or to inject the preparation of active compound, or the active compound itself, into the soil. The seeds of the plants can also be treated.

In the treatment of parts of plants, the active compound concentrations in the use forms can be varied within a substantial range: They are, in general, between 1 and 0.0001% by weight, preferably between 0.5 and 0.001% by weight.

In the treatment of seed, amounts of active compound of from 0.001 to 50g, preferably 0.01 to 10 g, are generally required per kilogram of seed.

In the treatment of the soil, active compound concentrations of from 0.00001 to 0.1% by weight, preferably from 0.0001 to 0.02% by weight, are required at the site of action.

The compositions which are used for protecting industrial materials contain the active compounds generally in an amount of from 1 to 95%, preferably of from 10 to 75%.

The use concentrations of the active compounds which are to be used according to the invention depend on the nature and the occurrence of the microorganisms to be controlled and also on the composition of the material to be protected. The optimum amount to be employed can be determined by test series. Generally, the. use concentrations are in the range of from 0.001 to 5% by weight, preferably from 0.05 to 1.0% by weight, based on the material to be protected.

The effectiveness and activity the spectrum of the active compounds which are to be used according to the invention in the protection of materials, or of the compositions, concentrates or quite generally formulations which can be prepared therefrom, can be increased by adding, if appropriate, further compounds having antimicrobial action, fungicides, bactericides, herbicides, insecticides or other active compounds to widen the activity spectrum or to obtain particular effects, such as, for example, the additional protection against insects. These mixtures may have a broader activity spectrum than the compounds which can be used according to the invention.

When used against animal pests, too, the substances which can be used according to the invention, in commercially available formulations and also in the use forms prepared from these formulations, can be present as a mixture with synergists. Synergists are compounds which enhance the effectiveness of the active compounds, without it being necessary for the synergist which is added to be active itself.

The content of active compound in the use forms prepared from the commercially available formulations can vary within wide ranges. The concentration of active compound in the use forms can be from 0.0000001 to 95% by weight of active compound, preferably between 0.0001 and 1% by weight.

Application is carried out in a manner which is appropriate for the use forms.

In the veterinary sector, the active compounds which can be used according to the invention are used in a known manner by enteral administration, for example in the form of tablets, capsules, drinks, drenches, granules, pastes, boluses, the feed-through method, suppositories, by parenteral administration, such as, for example, by means of injections (intramuscular, subcutaneous, intravenous, intraperitonal and the like), implants, by nasal application, by dermal administration, for example in the form of dipping or bathing, spraying, pouring-on and spotting-on, washing, dusting, and with the aid of shaped articles which comprise active compound, such as collars, eartags, tail marks, limb bands, halters, marking devices and the like.

When administered to livestock, poultry, domestic animals and the like, the active compounds can be used as formulations (for example powders, emulsions, flowables) which comprise the active compounds in an amount of from 1 to 80% by weight, either directly or after dilution by a factor of 100 to 10,000, or they may be used in the form of a chemical bath.

If the substances which are to be used according to the invention are employed as insecticides for protecting wood and timber products, the concentrates or the ready-to-use formulations generally comprise the active compounds in concentrations of between 0.0001 and 95% by weight, preferably between 0.001 and 60% by weight.

The amount of the compositions or concentrates employed depends on the nature and the occurrence of the insects and on the medium. For use, the optimum amount to be employed can in each case be determined by test series. In general, however, it is sufficient to employ from 0.001 to 20% by weight, preferably from 0.001 to 10% by weight, of the active compound, based on the material to be protected.

A particularly effective protection of wood with the aid of active compounds according to the invention is achieved by using large-scale industrial impregnation processes, for example vacuum, double-vacuum or pressure processes.

The ready-to-use compositions may comprise further insecticides and/or fungicides. Particularly preferred components which may be admixed are insecticides, such as chlorpyriphos, phoxim, silafluofin, alphamethrin, cyfluthrin, cypermethrin, deltamethrin, permethrin, imidacloprid, NI-25, flufenoxuron, hexaflumuron and triflumuron, and also fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The preparation and the use of active compounds which are to be used according to the invention is illustrated by the examples below.

PREPARATION EXAMPLES

Example 1

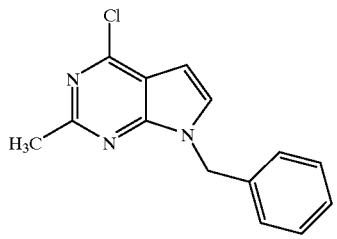

1.3 g (0.01 mol) of benzyl chloride are added to a suspension of 1.7 g (0.01 mol) of 4-chloro-2-methyl-7H-pyrrolo[2,3-d]pyrimidine and 2.1 g (0.015 mol) of potassium carbonate, and the mixture is heated at reflux for 18 hours. The reaction mixture is allowed to cool to room temperature and then concentrated under reduced pressure. The residue that remains is taken up in 200 ml of dichloromethane. The resulting mixture is washed with 100 ml of water and then dried over sodium sulphate and concentrated under reduced pressure. This gives 2.0 g (78% of theory) of 7-benzyl-4-chloro-2-methyl-7H-pyrrolo[2,3-d]pyrimidine in the form of an oil.

$^1$H-NMR: δ=2.77 (s, 3H); 5.42 (s, 2H); 6.54 (d, 1H); 7.08 (d, 1H) ppm.

The substances listed in Table 1 are also prepared following the procedures given in Example 1 and in the description.

TABLE 1

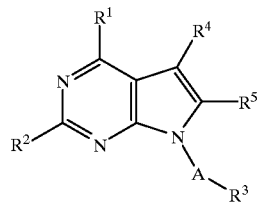

(I)

| Example No. | R¹ | R² | A | R³ | R⁴ | R⁵ | Physical data |
|---|---|---|---|---|---|---|---|
| 2 | —Cl | —CH₃ | —CH₂— | 4-chlorophenyl | H | H | mp.: 87° C. |
| 3 | —Cl | —CH₃ | —CH₂— | 3-chlorophenyl | H | H | mp.: 83° C. |
| 4 | —Cl | —CH₃ | —CH₂—CH₂— | Phenyl | H | H | NMR: 2.76(s, 3H); 3.12(t, 2H); 4.47(t, 2H)* |
| 5 | —Cl | —CH₃ | —CH₂— | 4-t-butylphenyl | H | H | NMR: 1.29(s, 9H); 2.78(s, 3H); 5.39(s, 2H)* |
| 6 | —Cl | —CH₃ | —CH₂—CH₂—O—**) | Phenyl | H | H | mp.: 70° C. |
| 7 | —Cl | —CH₃ | —CH₂—CH₂— | 4-t-butylphenyl | H | H | NMR: 1.30(s, 9H); 2.75 (s, 3H)* |
| 8 | —Cl | —CH₃ | —CH₂—CH₂—O—**) | 2,6-dichlorophenyl | H | H | mp.: 121° C. |
| 9 | —Cl | —CH₃ | —CH₂—CH₂— | Nitrophenyl | H | H | mp.: 144° C. |
| 10 | —Cl | —S—CH₃ | —CH₂— | Phenyl | H | H | mp.: 54° C. |
| 11 | —Cl | —S—CH₃ | —CH₂— | 4-chlorophenyl | H | H | mp.: 104° C. |
| 12 | —Cl | —S—CH₃ | —CH₂— | 3-chlorophenyl | H | H | mp.: 92° C. |
| 13 | —Cl | —S—CH₃ | —CH₂— | 4-t-butylphenyl | H | H | NMR: 1.29(s, 9H); 2.63(s, 3H); 5.34(s, 2H)* |
| 14 | —Cl | —CH₃ | —CH₂— | 4-t-butoxycarbonyl-phenyl | H | H | mp.: 127° C. |
| 15 | —Cl | —S—CH₃ | —CH₂— | 4-t-butoxycarbonyl-phenyl | H | H | mp.: 110° C. |
| 16 | —Cl | —H | —CH₂— | 4-chlorophenyl | H | H | mp.: 123° C. |
| 17 | —Cl | —H | —CH₂— | Phenyl | H | H | mp.: 63° C. |
| 18 | —Cl | —H | —CH₂— | 3-chlorophenyl | H | H | mp.: 96° C. |
| 19 | —Cl | —H | —CH₂— | 4-t-butyl-phenyl | H | H | mp.: 89° C. |
| 20 | —Cl | —H | —CH₂— | 4-t-butoxycarbonyl-phenyl | H | H | mp.: 104° C. |
| 21 | —Cl | —CH₃ | —CH₂—CH₂—O—**) | 4-bromophenyl | H | H | mp.: 121° C. |
| 22 | —Cl | —CH₃ | —CH₂—CH₂—O—**) | 2-methoxyphenyl | H | H | mp.: 93° C. |
| 25 | —O—CH₃ | —CH₃ | —CH₂— | Phenyl | H | H | mp.: 49° C. |
| 26 | —O—CH₃ | —CH₃ | —CH₂— | 3-trifluormethylphenyl | H | H | mp.: 58° C. |
| 27 | —O—CH₃ | —CH₃ | —CH₂— | 3-chlorophenyl | H | H | mp.: 51° C. |
| 28 | —O—CH₃ | —CH₃ | —CH₂— | 4-chlorophenyl | H | H | mp.: 97° C. |
| 29 | —Cl | —H | —CH₂— | 4-trimethylsilylphenyl | H | H | NMR: 0.00(s, 9H); 5.21(s, 2H); 8.43(s, 1H)* |
| 30 | —Cl | —CH₃ | —CH₂— | 4-trimethylsilylphenyl | H | H | NMR: 0.00(s, 9H); 2.53(s, 3H); 5.17(s, 2H)* |
| 31 | —O—CH₃ | —CH₃ | —CH₂— | 4-trimethylsilylphenyl | H | H | NMR: 0.00(s, 9H); 2.44(s, 3H); 3.86(s, 3H); 5.15(s, 2H)* |
| 32 | —Cl | —CH₃ | —CH₂— | 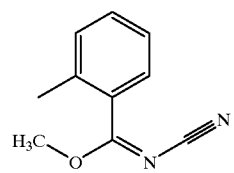 | H | H | mp.: 115° C. |

TABLE 1-continued

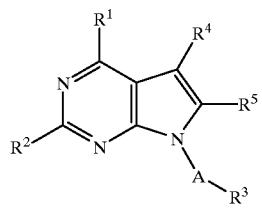

(I)

| Example No. | R¹ | R² | A | R³ | R⁴ | R⁵ | Physical data |
|---|---|---|---|---|---|---|---|
| 33 | —O—CH₃ | —CH₃ | —CH₂— | 2-methylphenyl with OCH₃ and N—C≡N group (methyl (E)-2-methyl-α-(cyanoimino)benzeneacetate) | H | H | mp.: 120° C. |
| 34 | —Cl | —CH₃ | —CH₂— | 6-chloro-3-pyridyl | H | H | mp.: 113° C. |
| 35 | —O—CH₃ | —CH₃ | —CH₂— | 6-chloro-3-pyridyl | H | H | NMR: 2.66(s, 3H); 4.11(s, 3H); 5.38(s, 2H)* |
| 36 | —Cl | —H | —CH₂— | 6-chloro-3-pyridyl | H | H | mp.: 122° C. |
| 37 | —Cl | —CH₃ | —CH₂—CH₂—O— | 4-chlorophenyl | H | H | mp.: 122° C. |
| 38 | —Cl | —CH₃ | —CH₂—CH₂—O— **) | 4-methoxyphenyl | H | H | mp.: 86° C. |
| 39 | —Cl | —CH₃ | —CH₂—CH₂—O— **) | 2,4-dichlorophenyl | H | H | mp.: 114° C. |
| 40 | —Cl | —CH₃ | —CH₂— | 4-methylphenyl-O-4-(tert-pentyl)phenyl | H | H | NMR: 0.68(t, 3H); 1.28(s, 3H); 1.42(s, 3H); 1.62(q, 2H); 2.75(s, 3H)* |
| 41 | —O—CH₃ | —CH₃ | —CH₂—CH₂—O— **) | 4-chlorophenyl | H | H | mp.: 79° C. |
| 42 | —O—CH₃ | —CH₃ | —CH₂—CH₂—O— **) | 4-methoxyphenyl | H | H | mp.: 85° C. |
| 43 | —O—CH₃ | —CH₃ | —CH₂—CH₂—O— **) | 2,4-dichlorophenyl | H | H | mp.: 90° C. |
| 44 | —O—CH₃ | —CH₃ | —CH₂— | 4-methylphenyl-O-4-(tert-pentyl)phenyl | H | H | NMR: 2.66(s, 3H); 4.09(s, 3H); 5.36(s, 2H)* |

TABLE 1-continued
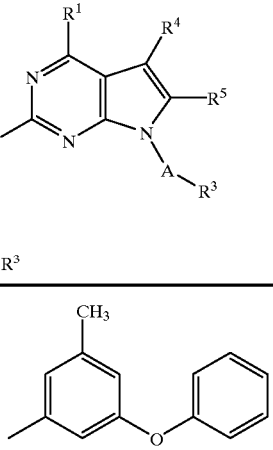
| Example No. | R¹ | R² | A | R³ | R⁴ | R⁵ | Physical data |
|---|---|---|---|---|---|---|---|
| 45 | —O—CH₃ | —CH₃ | —CH₂— | 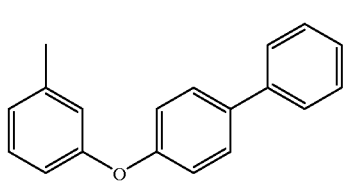 | H | H | NMR: 2.66(s, 3H); 4.10(s, 3H); 5.32(s, 2H)* |
| 46 | —O—CH₃ | —CH₃ | —CH₂— | 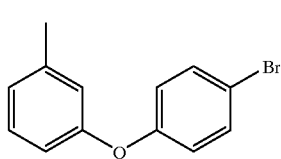 | H | H | NMR: 2.65(s, 3H); 4.08(s, 3H); 5.38(s, 2H)* |
| 47 | —O—CH₃ | —CH₃ | —CH₂— | 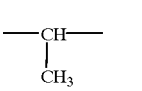 | H | H | NMR: 2.65(s, 3H); 4.10(s, 3H); 5.37(s, 2H)* |
| 48 | —Cl | —CH₃ | —(CH₂)₆—O— **) | 2-chloro-4-methoxyphenyl | H | H | NMR: 2.63(s, 3H); 3.72 (s, 3H)* |
| 49 | —Cl | —CH₃ | —(CH₂)₆—O— **) | 2.5-dimethylphenyl | H | H | NMR: 2.05(s, 3H); 2.24(s, 3H); 2.63(s, 3H)* |
| 50 | —Cl | H | 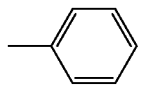 | 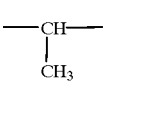 | H | H | HPLC***): Rf = 889 UV: λ_max = 226 nm |
| 51 | —Cl | H | 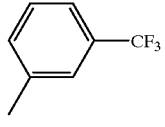 | 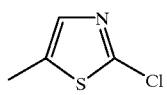 | H | H | HPLC***): Rf = 990 UV: λ_max = 224 nm |
| 52 | —Cl | H | —CH₂— | 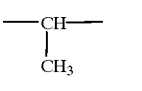 | H | H | mp. 96° C. |
| 53 | —Cl | —CH₃ | 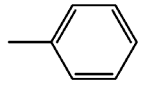 | 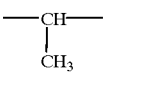 | —Cl | H | HPLC***): Rf = 1073 UV: λ_max = 232 nm |
| 54 | —Cl | —CH₃ | 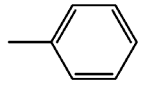 | 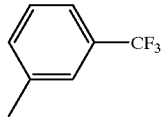 | —Cl | H | HPLC***): Rf = 1158 UV: λ_max = 232 nm |

TABLE 1-continued

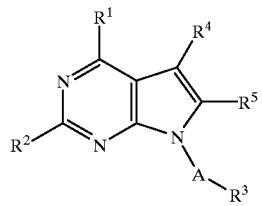

(I)

| Example No. | R¹ | R² | A | R³ | R⁴ | R⁵ | Physical data |
|---|---|---|---|---|---|---|---|
| 55 | —Cl | —CH₃ | —CH₂— | 4-chlorophenyl | —Cl | H | mp. 129° C. |
| 56 | —Cl | —CH₃ | —CH(CH₃)— | phenyl | H | H | HPLC***): Rf = 951<br>UV: $\lambda_{max}$ = 228 nm |
| 57 | —Cl | —CH₃— | —CH(CH₃)— | 3-(trifluoromethyl)phenyl | H | H | HPLC***): Rf = 1053<br>UV: $\lambda_{max}$ = 226 nm |
| 58 | —Cl | —CH₃ | —CH₂— | 2-chloro-5-methylthiazolyl | H | H | mp.: 90° C. |
| 59 | —Cl | —CH₃ | —CH₂—CH₂—SO₂—) | 4-chlorophenyl | | | HPLC*): Rf = 770<br>UV: $\lambda_{max}$ = 226 nm |
| 60 | —Cl | —H | —CH(CH₃)— | 4-chlorophenyl | —H | —H | HPLC***): Rf = 978 |
| 61 | —Cl | —H | —CH(CH₃)— | 4-fluorophenyl | —H | —H | HPLC***): Rf = 895 |
| 62 | —Cl | —H | —CH(CH₃)— | 2,6-dichlorophenyl | —H | —H | HPLC***): Rf = 1040 |
| 63 | —Cl | —H | —CH₂— | 5-chloro-3-methyl-1,2,4-thiadiazolyl | —H | —H | HPLC***): Rf = 709 |
| 64 | —Cl | —CH₃ | —CH(CH₃)— | 4-chlorophenyl | —H | —H | HPLC***): Rf = 1045 |
| 65 | —Cl | —CH₃ | —CH(CH₃)— | 4-fluorophenyl | —H | —H | HPLC***): Rf = 957 |
| 66 | —Cl | —CH₃ | —CH(CH₃)— | 2,6-dichlorophenyl | —H | —H | HPLC***): Rf = 1138 |

TABLE 1-continued

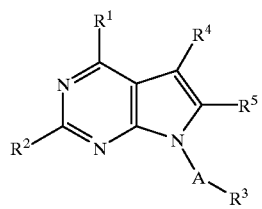
(I)

| Example No. | R¹ | R² | A | R³ | R⁴ | R⁵ | Physical data |
|---|---|---|---|---|---|---|---|
| 67 | —Cl | —H | —CH₂— | (3-methyl-1,3,4-thiadiazol-2-yl attached to 4-chloropyrrolo[2,3-d]pyrimidin-7-yl) | —H | —H | HPLC***): Rf = 915 |
| 68 | —Cl | —CH₃ | —CH₂— | (3-methyl-1,3,4-thiadiazol-2-yl attached to 4-chloropyrrolo[2,3-d]pyrimidin-7-yl) | —H | —H | HPLC***): Rf = 1057 |
| 69 | —Cl | —CH₃ | —CH₂— | (5-chloro-3-methyl-1,3,4-thiadiazol-2-yl) | —H | —H | HPLC***): Rf = 758 |

*)The ¹H-NMR spectra were recorded in deuterochloroform (CDCl) or hexadeuterodimethyl sulphoxide (DMSO-d₆) using tetramethylsilane (TMS) as internal standard. Stated is the chemical shift as δ value in ppm.
)The atom labelled  is in each case attached to the radical R³.
***)In the HPLC analysis, the retention index (Rf) was determined based on the 2-alkanones (C-3 to C-16) on a C-18 reversed phase HPLC using the gradient system phosphoric acid (0.1% strength)/acetonitrile.

USE EXAMPLES

Example A

Plasmopara Test (grape vines)/protective

Solvent: 47 parts by weight of acetone
Emulsifier: 3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating is dried on, the plants are inoculated with an aqueous spore suspension of plasmopara viticola and then remain in an incubation cabin at 20° C. and 100% relative atmospheric humidity for 1 day. The plants are subsequently placed in a greenhouse at 21° C. and approximately 90% atmospheric humidity for 5 days. The plants are then moistened and placed in [lacuna] incubation cabin for 1 day.

Evaluation is carried out 6 days after the inoculation. 0% means an efficacy which corresponds to that of the untreated control, while an efficacy of 100% means that no infection is observed.

Active compounds, active compound concentrations and test results are shown in the table below.

TABLE A

Plasmopara test (grape vine)/protective

| Active compound According to the invention: | Efficacy in % at a concentration of active compound in the spray liquor of 100 ppm |
|---|---|
| 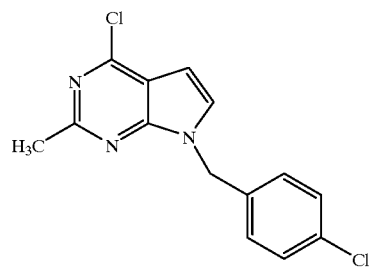 (2) | 90 |

TABLE A-continued

Plasmopara test (grape vine)/protective

| Active compound According to the invention: | Efficacy in % at a concentration of active compound in the spray liquor of 100 ppm |
|---|---|
| (22) [structure: 4-chloro-2-methyl-7-(2-(2-methoxyphenoxy)ethyl)-7H-pyrrolo[2,3-d]pyrimidine] | 85 |
| (24) [structure: 4-methoxy-2-methyl-7-(2-(2-methoxyphenoxy)ethyl)-7H-pyrrolo[2,3-d]pyrimidine] | 83 |

Example B
Podosphaera Test (apple)/protective

Solvent: 47 parts by weight of acetone
Emulsifier: 3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are inoculated with an aqueous spore suspension of the causative organism of apple mildew, *Podosphaera leucotricha*.

The plants are then placed in a greenhouse at 23° C. and a relative atmospheric humidity of approximately 70%.

Evaluation is carried out 10 days after the inoculation. 0% means an efficacy which corresponds to that of the untreated control, while an efficacy of 100% means that no infection is observed.

Active compounds, active compound concentrations and test results are shown in the table below.

TABLE B

Podosphaera test (apple)/protective

| Active compound According to the invention: | Efficacy in % at a concentration of active compound in the spray liquor of 100 ppm |
|---|---|
| (2) [structure: 4-chloro-2-methyl-7-(4-chlorobenzyl)-7H-pyrrolo[2,3-d]pyrimidine] | 100 |

Example C
Venturia Test (apple)/protective

Solvent: 47 parts by weight of acetone
Emulsifier: 3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are inoculated with an aqueous conidia suspension of the causative organism of apple scab, *Venturia inaequalis* and then remain in an incubation cabin at 20° C. and 100% relative atmospheric humidity for 1 day.

The plants are then placed in a greenhouse at 20° C. and a relative atmospheric humidity of approximately 70%.

Evaluation is carried out 10 days after the inoculation. 0% means an efficacy which corresponds to that of the untreated control, while an efficacy of 100% means that no infection is observed.

Active compounds, active compound concentrations and test results are shown in the table below.

TABLE C

Venturia test (apple)/protective

| Active compound According to the invention: | Efficacy in % at a concentration of active compound in the spray liquor of 100 ppm |
|---|---|
| ![compound 2: 4-chloro-2-methyl-7-(4-chlorobenzyl)-7H-pyrrolo[2,3-d]pyrimidine] (2) | 91 |

Example D
Leptosphaeria Nodorum Test (wheat)/protective

Solvent: 10 parts by weight of N-methyl-pyrrolidone

Emulsifier: 0.6 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate.

After the spray coating has dried on, the plants are sprayed with a spore suspension of *Leptosphaeria nodorum*. The plants remain in an incubation cabin at 20° C. and 100% relative atmospheric humidity for 48 hours.

The plants are placed in a greenhouse at a temperature of approximately 20° C. and a relative atmospheric humidity of approximately 80%.

Evaluation is carried out 10 days after the inoculation. 0% means an efficacy which corresponds to that of the untreated control, while an efficacy of 100% means that no infection is observed.

Active compounds, active compound concentrations and test results are shown in the table below.

TABLE D

Leptosphaeria nodorum test (wheat)/protective

| Active compound According to the invention: | Application rate of active compound in g/ha | Efficacy in % |
|---|---|---|
| ![compound 2] (2) | 250 | 100 |

Example E
Phaedon Larvae Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are populated with mustard beetle larvae (*Phaedon cochleariae*) while the leaves are still moist.

After the desired period of time, the kill in % is determined. 100% means that all beetle larvae have been killed; 0% means that none of the beetle larvae have been killed.

Active compounds, active compound concentrations and test results are shown in the table below.

TABLE E (plant-damaging insects)
Phaedon larvae test

| Active compound According to the invention: | Concentration of active compound in the spray liquor in % | Kill in % after 7 d |
|---|---|---|
| ![compound 2] (2) | 0.1 | 100 |

TABLE E-continued (plant-damaging insects)
Phaedon larvae test

| Active compound According to the invention: | Concentration of active compound in the spray liquor in % | Kill in % after 7 d |
|---|---|---|
| (3) [4-chloro-2-methyl-7-(3-chlorobenzyl)-7H-pyrrolo[2,3-d]pyrimidine] | 0.1 | 100 |
| (6) [4-chloro-2-methyl-7-(2-phenoxyethyl)-7H-pyrrolo[2,3-d]pyrimidine] | 0.1 | 100 |
| (26) [4-methoxy-2-methyl-7-(3-trifluoromethylbenzyl)-7H-pyrrolo[2,3-d]pyrimidine] | 0.1 | 100 |
| (41) [4-methoxy-2-methyl-7-(2-(4-chlorophenoxy)ethyl)-7H-pyrrolo[2,3-d]pyrimidine] | 0.1 | 100 |

TABLE E-continued
(plant-damaging insects)
Phaedon larvae test
| Active compound According to the invention: | Concentration of active compound in the spray liquor in % | Kill in % after 7 d |
|---|---|---|
| 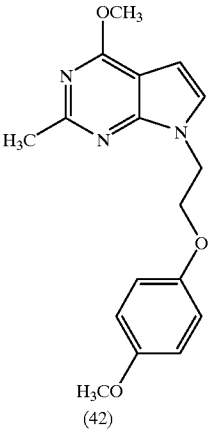 (42) | 0.1 | 100 |
| 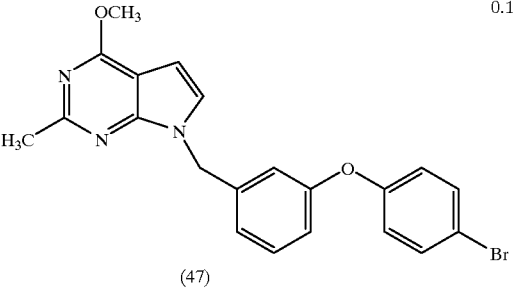 (47) | 0.1 | 100 |
| 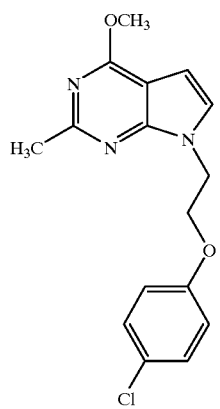 (41) | 0.1 | 100 |

-continued

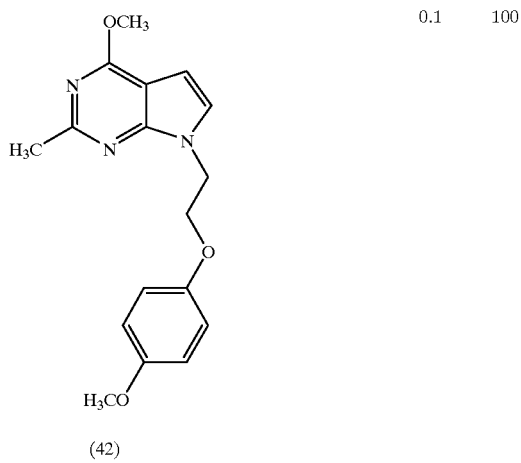

(42)   0.1   100

(47)   0.1   100

Example F
Plutella Test

Solvent: 7 parts by weight of dimethylfomamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are populated with caterpillars of the diamond-backed moth (*Plutella xylostella*) while the leaves are still moist.

After the desired period of time, the kill in % is determined. 100% means that all caterpillars have been killed; 0% means that none of the caterpillars have been killed.

Active compounds, active compound concentrations and test results are shown in the table below.

TABLE F

| (plant-damaging insects) Plutella test | | |
|---|---|---|
| Active compound According to the invention: | Concentration of active compound in the spray liquor in % | Kill in % after 7 d |
| 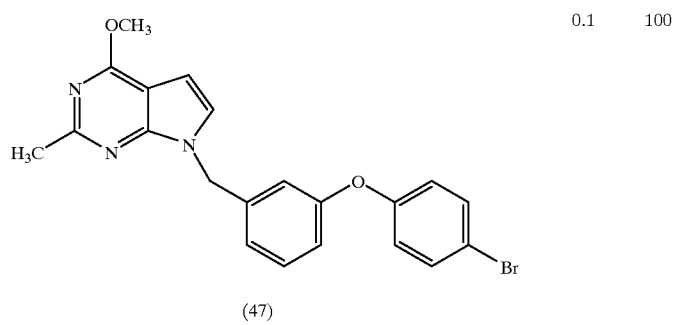 (2) | 0.1 | 100 |

TABLE F-continued (plant-damaging insects)
Plutella test

| Active compound According to the invention: | Concentration of active compound in the spray liquor in % | Kill in % after 7 d |
|---|---|---|
| 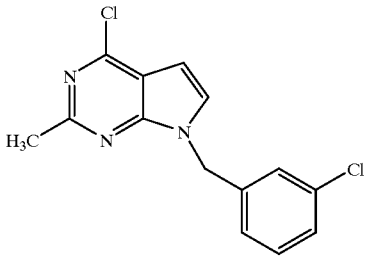 (3) | 0.1 | 100 |
| 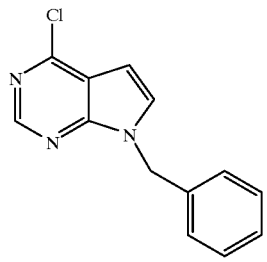 (17) | 0.1 | 100 |

Example G

Nephotettix Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Rice seedlings (*Oryza sativa*) are treated by being dipped into the preparation of active compound of the desired concentration and are populated with caterpillars of the green rice leaf hopper (*Nephotettix cincticeps*) while the seedlings are still moist.

After the desired period of time, the kill in % is determined. 100% means that all leaf hoppers have been killed; 0% means that none of the leaf hoppers have been killed.

Active compounds, active compound concentrations and test results are shown in the table below.

TABLE G (plant-damaging insects)
Nephotettix test

| Active compound According to the invention: | Concentration of active compound in the spray liquor in % | Kill in % after 6 d |
|---|---|---|
| 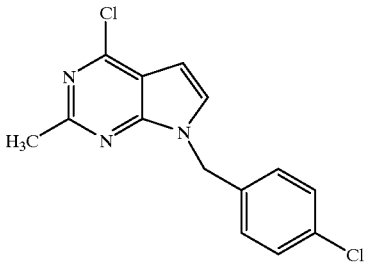 (2) | 0.1 | 100 |

TABLE G-continued (plant-damaging insects)

Nephotettix test

| Active compound According to the invention: | Concentration of active compound in the spray liquor in % | Kill in % after 6 d |
|---|---|---|
| (8) | 0.1 | 100 |
| (25) | 0.1 | 100 |
| (26) | 0.1 | 100 |
| (30) | 0.1 | 100 |

TABLE G-continued (plant-damaging insects)
Nephotettix test

| Active compound According to the invention: | Concentration of active compound in the spray liquor in % | Kill in % after 6 d |
|---|---|---|
| 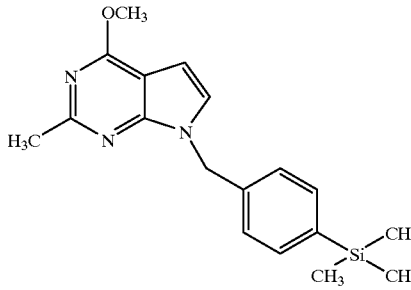 (31) | 0.1 | 100 |
| 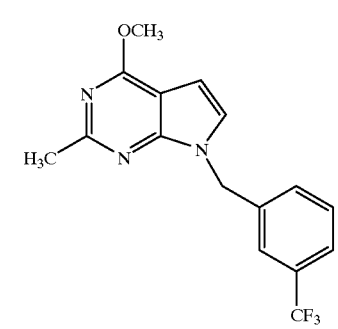 (26) | 0.1 | 100 |
| 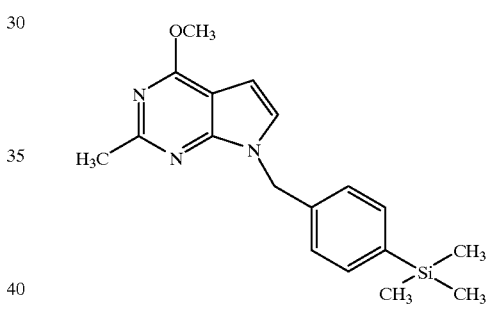 (30) | 0.1 | 100 |

-continued

| | 0.1 | 100 |
|---|---|---|
| 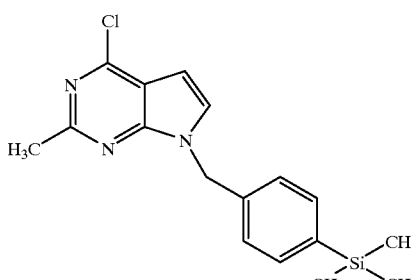 (31) | | |

Example H

Tetranychus Test (OP resistant/dip treatment)

Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with emulsifier-containing water to the desired concentration.

Bean plants (*Phaseolus vulgaris*) which are heavily infested by all stages of the greenhouse red spider mite (*Tetranychus urticae*) are dipped into a preparation of active compound of the desired concentration.

After the desired period of time, the effect in % in determined. 100% means that all spider mites have been killed; 0% means that none of the spider mites have been killed.

Active compounds, active compound concentrations and test results are shown in the table below.

TABLE H
(plant-damaging insects)
Tetranychus test (OP-resistant/dip treatment)
| Active compound According to the invention: | Concentration of active compound in the spray liquor in % | Kill in % after 7 d |
|---|---|---|
| 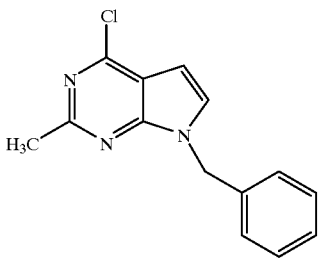 (1) | 0.1 | 100 |
| 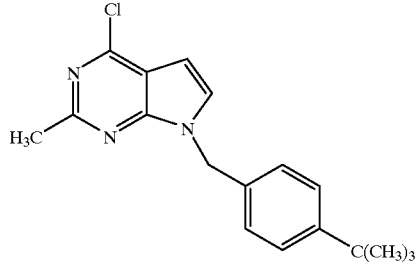 (5) | 0.1 | 100 |
| 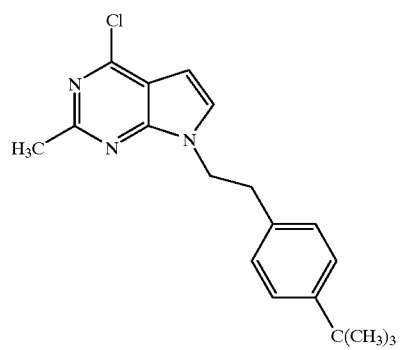 (7) | 0.1 | 100 |
| 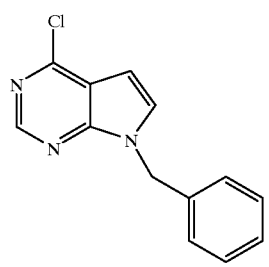 (17) | 0.1 | 100 |

TABLE H-continued
(plant-damaging insects)
Tetranychus test (OP-resistant/dip treatment)
| Active compound According to the invention: | Concentration of active compound in the spray liquor in % | Kill in % after 7 d |
|---|---|---|
| (26) 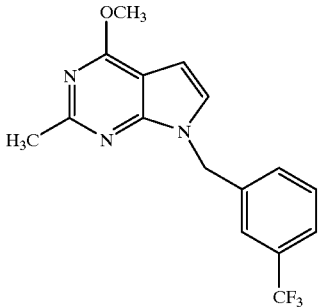 | 0.1 | 100 |
| (30) 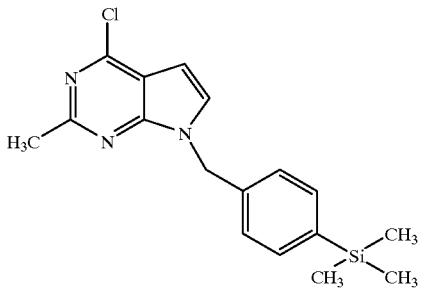 | 0.1 | 100 |
| (31) 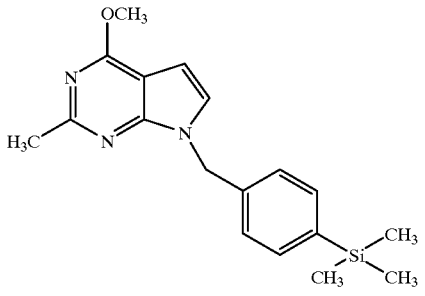 | 0.1 | 100 |
| (17) 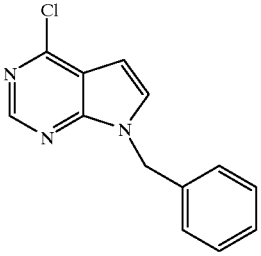 | 0.1 | 100 |
| (26) 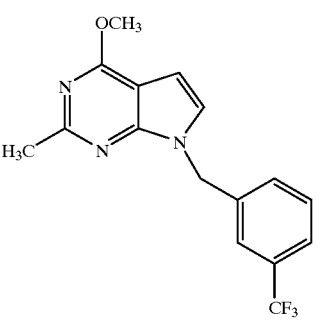 | 0.1 | 100 |

-continued

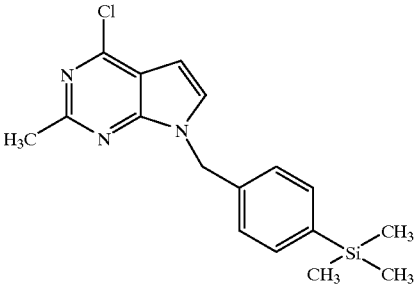

(30)

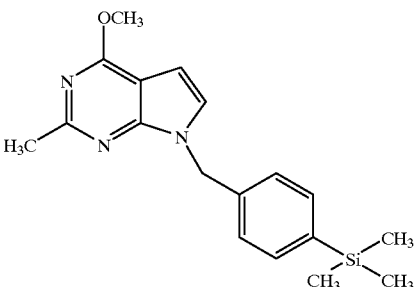

(31)

What is claimed is:

1. A method for controlling undesired microorganisms and animal pests, comprising the step of applying an effective amount of a pyrrolopyrimidine of the formula (I)

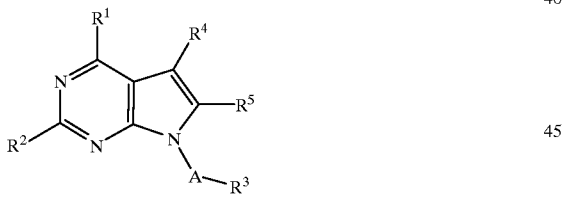

(I)

wherein $R^1$ represents fluorine, chlorine, bromine, iodine, alkoxy having 1 to 4 carbon atoms or halogenoalkoxy having 1 to 4 carbon atoms and 1 to 5 identical or different halogen atoms, $R^2$ represents hydrogen, fluorine, chlorine, bromine, iodine, alkyl having 1 to 4 carbon atoms, halogenoalkyl having 1 to 4 carbon atoms and 1 to 5 identical or different halogen atoms, alkoxy having 1 to 4 carbon atoms, alkylthio having 1 to 4 carbon atoms, halogenoalkoxy having 1 to 4 carbon atoms and 1 to 5 identical or different halogen atoms or halogenoalkylthio having 1 to 4 carbon atoms and 1 to 5 identical or different halogen atoms, $R^3$ represents aryl having 6 to 10 carbon atoms or represents heteroaryl having 3 to 12 ring members, wherein each is unsubstituted or mono- to pentasubstituted by identical or different substituents selected from the group consisting of halogen, cyano, nitro, formyl, carbamoyl, thiocarbamoyl, alkyl, alkoxy, alkylthio, alkylsulphinyl or alkylsulphonyl having in each case 1 to 5 carbon atoms, trialkylsilyl having 1 to 5 carbon atoms in each alkyl moiety, alkenyl or alkenyloxy having in each case 2 to 4 carbon atoms, halogenoalkyl, halogenoalkoxy, halogenoalkylthio, halogenoalkylsulphinyl or halogenoalkylsulphonyl having in each case 1 to 4 carbon atoms and 1 to 5 identical or different halogen atoms, in each case straight-chain or branched halogenoalkenyl or halogenoalkenyloxy having in each case 2 to 4 carbon atoms and 1 to 5 identical or different halogen atoms, alkylcarbonyl, alkylcarbonyloxy, alkoxycarbonyl, alkylsulphonyloxy, hydroximinoalkyl, alkoximinoalkyl or cyanimino (alkoxy)alkyl having in each case 1 to 4 carbon atoms in the individual alkyl moieties;

and in each case doubly attached dioxyalkylene having 1 or 2 carbon atoms or alkylene having 3 or 4 carbon atoms with which is unsubstituted or mono- to tetrasubstituted by identical or different substituents selected from the group consisting of halogen, alkyl having 1 to 4 carbon atoms and halogenoalkyl having 1 or 2 carbon atoms and 1 to 5 identical or different halogen atoms, cycloalkyl having 3 to 6 carbon atoms, a radical of the formula

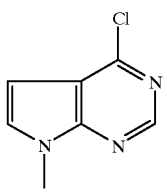

and phenyl or phenoxy, where these two radicals are unsubstituted or mono- to pentasubstituted by identical or different substituents selected from the group consisting of halogen, cyano, nitro, carbamoyl, thiocarbamoyl, alkyl having 1 to 5 carbon atoms, phenyl, halogenoalkyl having 1 to 4 carbon atoms and 1 to 5 identical or different halogen atoms, straight-chain or branched alkoxy or alkylthio having 1 to 4 carbon atoms, and straight-chain or branched halogenoalkoxy or halogenoalkylthio having 1 to 4 carbon atoms and 1 to 5 identical or different halogen atoms, and in each case doubly attached dioxyalkylene having 1 or 2 carbon atoms or alkylene having 3 to 4 carbon atoms which is unsubstituted or mono- to tetrasubstituted by identical or different substituents selected from the group consisting of halogen, alkyl having 1 to 4 carbon atoms and halogenoalkyl having 1 to 2 carbon atoms and 1 to 5 identical or different halogen atoms, $R^4$ and $R^5$ independently of one another each represent hydrogen, fluorine, chlorine, bromine, iodine or alkyl having 1 to 4 carbon atoms, and A represents alkanediyl having 1 to 8 carbon atoms or represents alkanediyl having 1 to 8 chain members, where 1 or 2 non-adjacent chain members are replaced by a heteroatom or heteroatom group selected from the group consisting of oxygen, sulphur and $SO_2$ and wherein a terminal oxygen or sulphur atom or an $SO_2$ group is in each case attached to a radical $R^3$.

* * * * *